US008227425B2

(12) United States Patent
Veronesi et al.

(10) Patent No.: US 8,227,425 B2
(45) Date of Patent: Jul. 24, 2012

(54) ANTIVIRAL COMPOUNDS (75) Inventors: Paolo Alberto Veronesi, Milan (IT);
Pablo Eduardo Andres Rodriguez,
Cordoba (AR); Emanuela Peschechera,
Milan (IT); Susanna Lucia Veronesi,
Milan (IT)

(73) Assignee: Therapicon Srl (IT)

( * ) Notice: Subject to any disclaimer, the term of this patent is extended or adjusted under 35 U.S.C. 154(b) by 385 days.

(21) Appl. No.: 12/524,216

(22) PCT Filed: Jan. 22, 2008

(86) PCT No.: PCT/EP2008/050703
§ 371 (c)(1),
(2), (4) Date: Jul. 23, 2009

(87) PCT Pub. No.: WO2008/090151
PCT Pub. Date: Jul. 31, 2008

(65) Prior Publication Data
US 2010/0029579 A1  Feb. 4, 2010

(30) Foreign Application Priority Data

Jan. 23, 2007  (IT) .................................. MI07A0093
Nov. 22, 2007  (IT) .................................. MI07A2212

(51) Int. Cl.
C07H 1/00 (2006.01)
C07H 15/00 (2006.01)
C07H 17/00 (2006.01)
C07H 5/04 (2006.01)
C07H 5/06 (2006.01)
C07G 3/00 (2006.01)
C07G 11/00 (2006.01)
C08B 37/00 (2006.01)
A01N 43/04 (2006.01)
A61K 31/70 (2006.01)

(52) U.S. Cl. ......... 514/23; 536/1.11; 536/4.1; 536/18.7; 514/25; 514/42; 514/33

(58) Field of Classification Search ............... 514/23, 514/25, 42, 33; 536/1.11, 4.1, 18.7
See application file for complete search history.

(56) References Cited

FOREIGN PATENT DOCUMENTS

| WO | WO 92/06691      | * | 4/1992 |
| WO | 00/29419 A1      |   | 5/2000 |
| WO | WO 2008/007153 A2 | * | 1/2008 |

OTHER PUBLICATIONS

Crich, D., Li, W. (2007) α-Selective Sialylations at −78 °C in Nitrile Solvents with a 1-Adamantanyl Thiosialoside. Journal of Organic Chemistry, vol. 72, p. 7794-7797.*
Buxton, R.C., Edwards, B., Juo, R.R., Voyta, J.C., Tisdale, M., Bethell, R.C. (2000) Development of a Sensisitve Chemiluminescent Neuraminidase Assay for the Determination of Influenza Virus Susceptibility to Zanamivir. Analytical Biochemistry, vol. 280, p. 291-300.*
European Patent Office, European Exam Report for EP Application No. 08 708 068.5, Sep. 27, 2011, 13 pages.
Babu, S. et al., "BCX-1812(RWJ-270201): Discovery of a Novel, Highly Potent, Orally Active, and Selective3 Influenza Neuraminidase Inhibitor through Structure-Based Drug Design", Journal of Medicinal Chemistry, vol. 43, No. 19, 2000, pp. 3482-3486.
Von Itzstein, et al., "Rational design of potent sialidase-based inhibitors of influenza virus replication", Nature, vol. 363, Jun. 3, 1993, pp. 418-423.
Aminoff, "Methods for Quantitative Estimation of N-Acetylneuraminic Acid and their Application to Hydrolysates of Sialomucoids", Biochem. J., vol. 81, 1961, pp. 384-392.
Miettinen, "use of Butyl Acetate in Determination of Sialic Acid", Acta Chem. Scand. 13, No. 4, 1959, pp. 856-858.
Svennerholm, "Quantitative Estimation of Sialic Acids II", Biochimica et Biophysica Acta, vol. 24, 1957, pp. 604-611.
Warren, "The Thiobarbituric Acid Assay of Sialic Acids", Journal of Biological Chemistry, vol. 234, No. 8, Aug. 1959, pp. 1971-1975.
Sweetman, Martindale: The Complete Drug Reference, 33rd Edition, May 2002, 8 pages.

* cited by examiner

*Primary Examiner* — Scarlett Goon
(74) *Attorney, Agent, or Firm* — Fellers, Snider, Blakenship, Bailey & Tippens, P.C.; Dennis D. Brown (57) ABSTRACT

The invention provides a new class of compounds exhibiting an inhibitory effect on neuraminidase (NA), hemagglutinin (HA) and structural $M_2$ protein bearing viruses. These compounds are also useful as inhibitors of the replication factors of hepatitis virus type C (HVC). The invention also describes pharmaceutical compositions containing the compounds of the invention either alone or in combination admixed with a suitable and pharmaceutically acceptable carrier.

12 Claims, 4 Drawing Sheets

Figure 1

(A) FT-IR (Fourier Transform Infrared Spectroscopy) spectrum of Compound 1.

(B) FT-IR spectrum of amantadine.

Figure 4

(A) FT-IR (Fourier Transform Infrared Spectroscopy) spectrum of Compound 10.

(B) FT-IR spectrum of ribavirine.

ANTIVIRAL COMPOUNDS

The present invention relates to a new class of chemical compounds useful as inhibitors of neuraminidase (NA), hemagglutinin (HA), the structural protein $M_2$ and hemagglutinin esterase fusion (HEF) glycoprotein; pharmaceutical compositions containing said compounds useful for the treatment, prevention or amelioration of viral infections; and methods of using said compounds and compositions.

It has been found that influenza viruses, when observed on an electronic microscope exhibit a spherical morphology with a diameter from 80 to 120 nm and/or a filamentous form (Yoshinori Fujiyoshi et al. "Fine structure if influenza A virus observed by electron cryo-microscopy", The EMBO Journal 13 (2), pages 318-26, 1994). The most typical characteristic of the viral membrane is the presence of radial projections that in the case of type A and B viruses correspond to haemoagglutinin (HA) and neuraminidase (NA) [(Wilson I. A. et al. "Structure of the haemoagglutinin membrane glycoprotein of influenza virus at 3 Å resolution", Nature, 289, pages 366-73, 1981; Varghese J. N. et al. "Structure of the influenza virus glycoprotein antigen neuraminidase at 2.9 Å resolution", Nature, 303, pages 35-40, 1983; Colman P. M. et al. "Structure of the catalytic and antigenic sites in influenza virus neuraminidase", Nature, 303, pages 41-44, 1983)] and in type C influenza virus to a glycoprotein named haemoagglutinin esterase fusion (HEF) responsible for three biological activities: binding to receptor (H), receptor inactivation (E) and fusion (F) (Herrier Georg, et al., "A synthetic sialic acid analogue is recognized by influenza C virus as a receptor but is resistant to the receptor-destroying enzyme", J. Biol. Chem., 2567 (8), pages 12501-12505, 1992).

The first generation antiviral products (mainly adamantane derivatives, alike amantadine, rimandadine and the like) are believed to act by blocking the $M_2$-protein ion-channel of influenza virus type A. Blocking the influx of $H^+$ ions through the $M_2$-proton channel inhibits uncoating and release of free ribonucleoproteins into the cytoplasm. This only occurs in the A strain of the virus, not the B strain.

Thereafter, antiviral strategy was directed to the development of second generation antivirals, such as zanamivir and oseltamivir, which inhibit either hemagglutinin (HA) or the enzyme neuraminidase (NA), which is present, as a mushroom-shape projection on the surface of influenza viruses type A and B. These proteins bind the surface of the membrane of the target cell to be infected by cleaving the sialic acid moieties of sialoglycoproteins and glycolipids. Furthermore, at the end of the viral replication the enzyme neuraminidase is essential to cleave sialic acid from receptors to allow viral release.

Current strategies to combat hepatitis type C virus (HVC), by contrast, involve inhibition using ribavirin (as monophosphate) at the synthesis of guanosin monophosphate, by reducing intracellular levels. Moreover rivabirin (as triphosphate) inhibits the enzyme ARNm-guanilyltranspherase by decreasing the synthesis of viral ARNm and also of ARN polymerase.

International publications are increasingly reporting both drug-resistant influenza strains and continuous mutations particularly of type A virus and resistant variants or combinations are transmissible and fully pathogenic. In this respect, during the most recent years the avian influenza A (H5N1) virus has been described by scientists as a serious risk of pandemic out-breaks.

Similarly, hepatitis type C infections are very common world-wide, thus also representing a serious pathogenic condition affecting an increasing number of patients.

In view of the above, there is an urgent need to develop improved antiviral compounds, preferably presenting a multiple-combined mechanism of action on the viral replication.

BRIEF DESCRIPTION OF RELATED ART

Itzstein, M. von et al.; "Nature", 363 (6428), pages 418-423 (1993), discloses the rational design of sialidase-based inhibitors of influenza virus replication. Colman, P. M. et al.; WO 92/06691 (PCT/AU90/00501, publication date Apr. 30, 1992), Itzstein, L. M. von et al.; EP 0539204A1 (European Application 92309684.6, publication date Apr. 28, 1993), and Itzstein, L. M. von et al.; WO 91/16320 (PCT/AU91/00161, publication date Oct. 31, 1991) disclose compounds that bind neuraminidase and are asserted to exhibit antiviral activity in vivo. Bischofberger N. W. et al.; U.S. Pat. No. 5,952,375 (U.S. application Ser. No. 08/606,624, application date Feb. 26, 1996) discloses novel compounds as neuraminidase inhibitors.

Babu Y. S., Chad P., Bantia S. et al.: "*Discovery of a novel, highly potent, orally active, and selective influenza neuraminidase inhibitor through structure-based drug design*". J Med Chem, 43(19): 3482 (2000), International Publication WO 99/33781 (Int. Appl. PCT/US98/26871, publication date Jul. 8, 1999) discloses novel substituted compounds and derivatives useful as neuraminidase inhibitors.

Furthermore, it is common medical practice, as described in Martindale 33.rd Ed. (2002) pages 639-43, to combine in human subjects the simultaneous administration of purine nucleoside analogues, such as ribavirin or viramidine, with a cytokine, such as interferon alpha-2b (or pegylated interferon alpha-2b) in order to treat chronic HVC infection. In fact, it is believed that ribavirin monophospahate and such derivatives inhibit the synthesis and the intracellular concentrations of guanosine monophosphate, while the triphosphate salt interferes with RNAm-guanilyltransferase.

OBJECT OF THE INVENTION

One object of the invention is to provide new chemical compounds exhibiting a significant inhibitory effect on viruses, and in particular on influenza and hepatitis viruses. The new compounds exert their combined and selective inhibition of the membrane protein, hemagglutinin (HA), on structural proteins, such as $M_2$ in viruses, and on the glycolitic enzymes, such as neuraminidase (NA), and more particularly via interference with viral neuraminidases. The novel compounds also exert an inhibitory activity on hepatitis virus type C (HVC). Another object is to provide improved and less expensive inhibitors of viral replication and of the transmission processes of the most common viruses responsible for severe viral infections, without any cross-resistance with the currently used antivirals. A still further object is to provide improved methods for administration of the novel compounds of the invention or of their rational combinations with other known antiviral agents. An additional object is to provide pharmaceutical compositions useful for the above purposes.

These and other objects will be readily apparent to the ordinary artisan from consideration of the invention as a whole.

SUMMARY OF THE INVENTION

In a first aspect of the present invention, a compound of general formula (I) is provided herein:

wherein:
X is —CH$_2$—, —O—, —CHF—, —CF$_2$—;
a single or double bond links C$_2$ to C$_3$ of the ring;
R$^1$ denotes —OH, an halogen or —B/moiety, but with the proviso that R$^1$ is absent when a double bond linking C$_2$ to C$_3$ of the ring is present; and
R$^2$ denotes —OH, —O—CH(C$_2$H$_5$)$_2$, —NH$_2$, —NHC(NH)NH$_2$ or —NH—OH; and
R$^3$ is —NH$_2$, —NHCO—CH$_3$ or —NH—CO—CH$_2$—OH; and
R$^4$ denotes —CHOH—CHOH—CH$_2$—OH, —CHOH—CH$_2$—B/moiety, —CH$_2$—B/moiety or —B/moiety
wherein —B/moiety denotes:

wherein:
R$^5$ denotes the linking function —NH—, —CH$_2$—NH—, —CH(CH$_3$)—NH—, —NH—CH(CH$_3$)—NH—, —C(CH$_3$)$_2$—CH$_2$—NH—, —NH—CO—CH$_2$—O—CH$_2$—CH$_2$—NH— or R$^6$ is —H, —CH$_3$ or —C$_2$H$_5$; and
R$^7$ is —H, —CH$_3$ or —C$_2$H$_5$; and
R$^8$ denotes the linking function —NH—, —CO—NH— or —C(NH)—NH—;
and their C1-4 carboxyl mono or poly esters, addition salts, solvates, resolved enantiomers and purified diastereomers thereof.

Also encompassed within the present invention are pharmaceutical compositions containing a compound of the invention either alone or in combination with other active agents in a pharmaceutically acceptable carrier suitable for administration to mammals, particularly humans.

In another embodiment of the invention the activity of neuraminidase and/or protein M$_2$ may be inhibited by a method comprising the step of treating a sample suspected of containing neuraminidase and/or protein M$_2$ with a compound or composition of the invention.

Another aspect of the invention provides a method for the treatment, or prevention of viral infections, for example caused by influenza virus or hepatitis virus, in a host comprising administration to the host by any suitable administration route of a therapeutically effective dose of a compound according to the invention described herein.

In other embodiments of the present invention, novel methods for the synthesis of the compounds of this invention are also provided.

DETAILED DESCRIPTION OF THE INVENTION

The present invention relates to compounds of structural formula (I) of the following configuration:

wherein:
X is —CH$_2$—, —O—, —CHF—, —CF$_2$—; and
a single or double bond links C$_2$ to C$_3$ of the ring; and
R$^1$ denotes —OH, an halogen or —B/moiety, but with the proviso that R$^1$ is absent when a double bond linking C$_2$ to C$_3$ of the ring is present; and
R$^2$ is —OH, —O—CH(C$_2$H$_5$)$_2$, —NH$_2$, —NHC(NH)NH$_2$ or —NH—OH; and
R$^3$ is —NH$_2$, —NHCO—CH$_3$ or —NH—CO—CH$_2$—OH; and
R$^4$ denotes —CHOH—CHOH—CH$_2$—OH, —CHOH—CH$_2$—B/moiety, —CH$_2$—B/moiety or —B/moiety
wherein —B/moiety denotes:

wherein:
R$^5$ denotes a linking function —NH—, —CH$_2$—NH—, —CH(CH$_3$)—NH—, —NH—CH(CH$_3$)—NH—, —C(CH$_3$)$_2$—CH$_2$—NH—, —NH—CO—CH$_2$—O—CH$_2$—CH$_2$—NH— or R$^6$ is —H, —CH$_3$ or —C$_2$H$_5$; and
R$^7$ is —H, —CH$_3$ or —C$_2$H$_5$; and
R$^8$ denotes a linking function —NH—, —CO—NH— or —C(NH)—NH—.

In a preferred embodiment X is denoted by —O—, typical of the sialic acid ring, where the carboxylic acid in C$_1$ remains unsubstituted, since it is believed to be the attraction point for viral neuraminadase. In another more preferred embodiment either a single or a double bond link $C_2$ to $C_3$ of the ring, with the proviso that, in presence of a double bond, $R^1$ is absent. In another typical embodiment at least either $R^1$ or $R^4$ may be mono-substituted by the —B/moiety. Therefore, $R^1$ preferably denotes —OH, halogen or typically a —B/moiety, while $R^4$ denotes either —CHOH—CHOH—$CH_2$—OH or a typical —CHOH—$CH_2$—B/moiety, wherein the —B/moiety may be either a —B1/moiety or a —B2/moiety.

When a typical —B1/moiety is used, a specific inhibition on the neuraminidase mechanism of A and B influenza virus strains is preferably elicited and a blockage of the $M_2$-protein ion-channel (present only in strain A) is also permitted. A —B2/moiety may also be used for a mono-substituted derivative, to achieve a similar inhibitory effect. In another suitable combination $R^1$ and $R^4$ may be identical or differently bisubstituted. In a preferred combination $R^1$ and $R^4$ may be both substituted by a —B2-moiety and the resulting compound is believed to inhibit more selectively the HVC replication.

When $R^1$ is substituted either by the —B1/moiety or —B2/moiety and $R^4$ is differently denoted as either being a —B2/moiety or —B1/moiety, it is believed that the resulting inhibition may affect both A and B influenza virus strains and also HVC.

In a further preferred combination $R^2$ may be —OH and $R^3$—NHCO—$CH_3$. When simultaneously $R^1$ or $R^4$ is substituted by a —B1/moiety linked to the main structure (I) another preferred embodiment is that the linking function $R^5$ may be —NH— or —CH($CH_3$)—NH—, while $R^6$ and $R^7$ may preferably be —H or —CH3. When $R^1$ or $R^4$ is denoted by a —B2/moiety linked to the main structure (I), the linking function $R^8$ may preferably be —CO—NH—.

Also, encompassed within the present invention are the linear or branched $C_{1-4}$ carboxyl mono or poly esters, addition salts, solvates, resolved enantiomers and purified diastereomers of the compounds of the invention.

In another embodiment of the invention, the activity of neuraminidase and/or of the $M_2$ ion-channel may be inhibited or blocked by treating a viral sample, suspected of containing neuraminidase and/or $M_2$ protein with a compound or a composition of the invention as described herein.

In another aspect the invention is directed to a method for the treatment or prophylaxis of viral infections, particularly from influenza A and B virus strains or of HVC, in a mammalian host comprising administration to the host by any suitable administration route of a therapeutically effective dose of a compound according to the invention.

In another embodiment, novel methods for the synthesis of the compounds of this invention are also provided.

Also encompassed within the present invention are pharmaceutical compositions containing a compound according to the invention either alone or in combination with, for example, another compound of the invention or one or more active agents in a pharmaceutically acceptable carrier thus rendering them suitable, for example, for administration to mammals.

A further aspect of the present invention comprises a method for the treatment or prophylaxis of said viral diseases or conditions by combining a treatment of mammals using a compound or of a pharmaceutical composition of the invention or a mixture thereof together with a simultaneous or alternate treatment with another therapeutically effective dose of an active agent also capable of inhibiting such viral infections.

Also embraced by the present invention are methods of producing the compounds of the invention. The compounds may be prepared by any of the applicable techniques of organic synthesis, which are well known to a skilled artisan.

For the general preparation of preferred compounds of the invention where $R^1$ is linked directly to $C_2$ of a sialic acid ring (X=—O—), the reductive amidation process, as initially described by Tang et al. Biochem. Biophys. Res. Commun., 132: 474-80 (1985) and modified by Stoll et al., Biochem. J., 256: 661-4 (1988) and by Scharzmann G. et al., Biochem., 22:5041-9 (1983), may be preferred. In fact, by following the above methods a covalent amine link between $C_2$ of the sialic ring and the amino group of —B/moiety may be established.

Similarly, for the general preparation of other preferred compounds of the invention, such as those where $R^4$ is linked directly to the $C_6$ of a sialic acid ring (X=—O—) many of the known techniques described in the following publications may be followed: Compendium of Organic Synthetic Methods (John Wiley & Sons, New York), Vol. 1, Ian T; Harrison and Shuye, Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr. 1984; and Vol. 6, Michael B. Smith; as well as March, J., 2Advanced Organic Chemistry, Third Edition, (John Wiley & Sons, New York, 1985), Comprehensive Organic Synthesis. Selectivity, Strategy & Efficacy in modern Organic Chemistry. In 9 Volumes, Barry M. Trost, Editor-in-Chief (Pergamon Press, New York, 1993 printing).

A number of exemplary methods for the preparation of the compounds of the invention are provided below, but they are not intended to limit the scope of applicable methods.

Generally, the reaction conditions such as temperature, reaction time, solvents, work up procedures, and the like, will be those common in the art for the particular reaction to be performed. The cited reference material, together with material cited therein, contains detailed descriptions of such conditions. As an exemplary method, the following general steps may be applicable to the general synthesis of $R^4$ substituted compounds of the invention.

Nevertheless, a skilled artisan would recognise that other standard procedures are available to yield the same materials.

Step 1—Preparation of Intermediate 1 of the Following Structure:

Intermediate 1

Treatment of sialic acid with Dowex 50 ($H^+$) in methanol with stirring, for a period of time 24-48 hours at reflux. The resin is filtered off and the filtrate is concentrated to dryness to yield the desired dimethyl substituted (Intermediate 1).

Step 2—Preparation of Intermediate 2 of the Following Structure:

Intermediate 2

The solid obtained from Step 1 is recovered with a sodium hydroxide aqueous solution and stirred at room temperature, generally during 1-3 hours. The mixture is then adjusted to pH 7.0-7.5 with Dowex 50 (H$^+$) resin. Filtration followed by freeze-drying of the filtrate yields the corresponding non methylated ester (Intermediate 2).

Step 3—Preparation of Intermediates 3 and 4 of the Following Structures:

Intermediate 3

Intermediate 4

The intermediate obtained from Step 2 is reacted in darkness during 1 hour with an aqueous solution of sodium metaperiodate in a different molar ratio to yield either Intermediate 3 (lower ratio) or Intermediate 4 (higher ratio). Barium acetate is then added to precipitate and eliminate by filtration the excess of iodate and periodate. The filtrate is then lyophilized. A yellowish solid is obtained (Intermediates 3 or 4).

Step 4—Preparation of Intermediate 5 and 6 of the Following Structure:

Intermediate 5

Intermediate 6

The resulting intermediates 3 or 4 from Step 3 are separately dissolved with an aqueous solution of formic acid under stirring and heated at 80° C. during 1 hour. The resulting solutions are individually lyophilized. Intermediates 6 and 5 are obtained respectively.

Step 5—Preparation of Final R$^4$ Mono-Substituted Compounds According to the Following Exemplary Reaction Schemes:

Scheme A

Intermediate 5    Reacting product generating a-B1/moiety

Compound 1

A R$^4$ mono-substituted (—B1/moiety) compound of the invention

Scheme B

Intermediate 6

Reacting product generating a -B2/moiety

Compound 2

Another R$^4$ mono-substituted (—B2/moiety) compound of the invention

Each resulting intermediate 5 or 6 from Step 4 is separately recovered with distilled water with the selected reacting product generating the desired —B/moiety (either —B1/moiety or —B2/moiety) and the reaction mixture is kept standing overnight at 4° C. Sodium borohydride is then added and the reaction mixture is kept standing at room temperature during 1 hour. Each sample is deionized on a Dowex 50 (H+) column and the elute is lyophilized separately to yield a different final compound of the invention.

Other typical R⁴ mono-substituted (with different —B/moiety) compounds of the invention are for instance represented hereby and are described in further Examples:

Compound 3

Compound 4

Compound 5

Compound 6

Compound 7

Compound 8

Compound 9

Compound 10

Another preferred production embodiment encompasses the synthesis of R¹ mono-substituted compound by using the following reaction steps:

Step 1—Preparation of a R¹ Mono-Substituted (—B/Moiety) Compound

Sialic acid is dissolved in a mixture of methanol and water in a different ratio (a 9:1 ratio is preferred) and a reacting product generating a —B/moiety is added under slight stirring. After addition of sodium borohydride the mixture is kept at 60° C. under slight stirring during 2 hours. The mixture is then passed on a Dowex 50 (H+) column to covert sodium borohydride into boric acid. The elute is lyophilized, recovered with small aliquots of methanol and passed a on paper filter. The residue is withdrawn and the elute is brought to dryness. The latter operation is repeated several times as required (generally more than 5 fold). The resulting solid is finally dissolved in a small aliquot of water and then lyophilised to yield the desired R¹ mono-substituted (with —B/moiety) compound of the invention.

Other typical reaction schemes may be represented as follows:

Scheme C

An $R^1$ mono-substituted (—B1/moiety) compound of the invention (Compound 11).

Scheme D

Another $R^1$ Mono-Substituted (—B2/Moiety) Compound of the Invention

Another further preferred production embodiment encompasses the synthesis of a $R^1$ and $R^4$ bi-substituted compound by adopting the following general reaction schemes:

Step 1—Preparation of $R^1$ and $R^4$ Bi-Substituted (—B/Moiety) Compound By combining the hereinabove described production schemes (A, B, C and D) a skilled artisan may yield a bi-substituted compound of the invention.

Typical final bi-substituted (with identical or different —B/moieties) compounds of the invention are represented hereby:

A typical $R^1$ and $R^4$ bi-substituted (with identical —B1/moiety) compound.

Another typical $R^1$ and $R^4$ bi-substituted (with identical —B2/moiety) compound.

It will be apparent to a skilled artisan that by using identical reacting product generating either a —B1/moiety or a —B2/moiety, each presenting the other possible combinations of $R^6$, $R^7$ and $R^8$ as represented in the general formula (I), it is possible to yield analogous bi-substituted compounds of the invention.

A typical $R^1$ and $R^4$ bi-substituted (with different combined —B/moieties) compound of the invention.

Another typical $R^1$ and $R^4$ bi-substituted (with different combined —B/moieties) compound of the invention.

Similarly, by using a different reacting product combining a —B1/moiety and a —B2/moiety, each presenting other possible combinations of $R^6$, $R^7$ and $R^8$ as represented in the general formula (I), it is possible to yield analogous different bi-substituted compounds of the invention.

It will also be apparent to a skilled artisan that the detection and the quantitative estimation of sialic acid by using the typical resorcinol-HCl method (Svennerholm L. "Quantitative estimation of sialic acids. II. A colorimetric resorcinol-hydrochloric acid method." Biochem. Biophys. Acta, 24 (3),: 604-611, 1957; Miettinen J. et al. "Use of butyl acetate in determination of sialic acid.", Acta Chem. Scand., 13, 856-858, 1959) and the TBA (2-thiobarbituric acid) method (Warren L. "The thiobarbituric acid assay of sialic acids.", J. Biol. Chem., 234, 1971-5, 1959; Aminoff D. "Methods for the quantitative estimation of N-acetylneuraminic acid and their application to hydrolysates of sialomucoids.", Biochem. J., 81 (2), 384-392, 1961) differ for the following reason: Resorcinol-HCl method allows to detect and to determine quantitatively sialic acid and its derivatives both when present in the free and when conjugated with other sugars, as for instance in the sialoglycocompounds. By contrast, TBA method allows to detect and to estimate quantitatively sialic acid and its derivatives only if the hydroxyl-moiety ($R_1$=—OH), linked to the carbon atom in position 2 ($C_2$), is not substituted.

The compounds of the invention also encompass enriched or resolved optical isomers at any or all asymmetric atoms. Both racemic and diasteromeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomers of the desired starting material.

The compositions of this invention optionally comprise salts of the compounds herein, especially pharmaceutically acceptable non-toxic salts containing for example inorganic or preferably organic acids or bases. Salification is a preferred procedure when water soluble salts of the compounds are desired.

Another aspect of the invention relates to methods of inhibiting the activity of neuraminidase comprising the step of treating a sample suspected of containing neuraminidase, for example viral neuraminidase, with a compound of the invention. The compounds of the invention are believed to act as inhibitors of neuraminidase, as intermediates for such inhibitors or have other utilities as described below. In fact, the inhibitors will bind to locations on the surface or in a cavity of neuraminidase having a geometry unique to neuraminidase. However, compounds binding neuraminidase may bind with varying degrees of reversibility. Those compounds binding substantially irreversibly are ideal candidates for use in the method of the invention. Organisms that contain neuraminidase include bacteria (Vibrio cholerae, Clostridium perfringens, Streptococcus pneumoniae, and Arthrobacter sialophilus) and viruses (especially orthomyxoviruses or paramyxoviruses such as influenza virus A and B, parainfluenza virus, rhinovirus, coronaviruses, mutant coronaviruses and/or modified coronaviruses, mumps virus, Newcastle disease virus, fowl plague virus, and Sendai virus). Inhibition of neuraminidase activity obtained from or found within any of these organisms is within the scope of the invention. The compounds of this invention are also useful in the treatment or prevention of such infections in animals, e.g. duck, rodents, or swine, or in man.

In a further embodiment, compounds of the invention are screened for inhibitory activity against neuraminidase by conventional techniques for evaluating enzyme activity. Within the context of the invention, typically compounds are first screened for inhibition of neuraminidase in vitro.

A further aspect of the invention relates to methods of blocking the influx of H+ ions through the M2-protein ion-channel, inhibiting uncoating and release of free ribonucleoproteins into the cytoplasm, comprising the step of treating with a compound of the invention a sample suspected of containing M2-protein, such as strain A influenza virus. In fact, compounds of the invention are also believed to act by blocking the viral M2-protein functions.

Another further aspect of the invention relates to methods of inhibiting the synthesis of guanosin monophosphate and the RNAm-guanilyltransferase comprising blocking the RNAm and RNA polymerase synthesis of HVC by treating the suspected sample with a compound of the invention.

In another embodiment, differently bi-substituted compounds of the invention are believed to act simultaneously as inhibitors of neuraminidase and of M2-proton ion channel.

The compounds of the present invention may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the reknown publication "Handbook of Pharmaceutical Excipients" $4^{th}$ Edition, Rowe R. C. et al., Pharmaceutical Press (2003). Excipients include ascorbic acid and other antioxidants, chelating agents such as EDTA, carbohydrates such as dextrin, hydroxyalkylcellulose, hydroxyalkylmethylcellulose, stearic acid and the like.

One or more compounds of the invention (hereinafter also referred to as the active ingredients) may be administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed as oral pharmaceutical forms; it is possible, but not necessary to administer them by intrapulmonary or intranasal routes.

While it is possible for the active ingredients of the invention to be administered alone it may be preferable to present them as pharmaceutical formulations. The formulations of the invention, which may be both for veterinary and for human use, comprise at least one active ingredient or compound of the invention, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy.

Techniques and formulations generally are found in "Remington's Pharmaceutical Sciences" Mack Publishing Co., Easton, Pa., U.S.A. Such methods include the step of bringing into association the active ingredient with the carrier which constitutes one or more accessory ingredients. In general the formulations may be prepared by uniformly and intimately bringing into association the active ingredient with liquid carriers or finely divided solid carriers or both, and then, if necessary, shaping the product as desired.

Formulations of the invention suitable for oral administration may be prepared as solid units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations may preferably be applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredient(s) may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may also desirably include a compound which enhances absorption or penetration of the active ingredient through the skin or other affected areas. Examples of such dermal penetration enhancers include dimethyl sulphoxide and related analogs. The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil.

Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain/esters known as Crodamol CAP may be used, the last three being preferred esters. These may be used alone or in combination depending on the properties required. Alternatively, high melting point lipids such as white soft paraffin are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 2.0% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size in the range of 0.1 to 500 microns (including particle sizes in a range between 0.1 and 500 microns in increments microns such as 0.5, 1, 30 microns, 35 microns, etc.), which are administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of influenza A or B infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilized) condition requiring only the addition of the sterile liquid carrier (solvents), for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The invention further provides veterinary compositions comprising at least one active ingredient as above defined together with a veterinary carrier therefore.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention may be used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

An effective dose of active ingredient depends at least on the nature of the condition being treated, toxicity, whether the compound is being used prophylactically (lower doses) or against an active influenza infection, the method of delivery, and the pharmaceutical formulation, and will be determined by the clinician using conventional dose escalation studies.

It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, for inhalation the daily candidate dose for an adult human of approximately 70 kg body weight will range from 1 mg to 1000 mg, preferably between 5 mg and >500 mg, and may take the form of single or multiple doses. Larger therapeutically effective daily dosages may be also administered when required by the pathological conditions of the subject.

Active ingredients (or compounds) of the invention are also used in combination with other active ingredients. Such combinations are selected based on the condition to be treated, cross-reactivities of ingredients and pharmacoproperties of the combination. For example, when treating viral infections of the respiratory system, in particular influenza infection, the compositions of the invention are combined with anti-virals (such as amantidine, rimantadine and ribavirin), mucolytics, expectorants, bronchialdilators, antibiotics, antipyretics, or analgesics. Ordinarily, antibiotics, antipyretics, and analgesics are administered together with the compounds of the invention.

The invention has been described in detail sufficient to allow one of ordinary skill in the art to make and use the subject matter of the following examples. It is apparent that certain modifications of the methods and compositions of the following examples can be made within the scope and spirit of the invention. The invention will be further described with reference to the following exemplary embodiments, and accompanying FIGS. 1-4 wherein:

EXAMPLES

Example 1

Preparation of Intermediate 1

225 mg of sialic acid (0.73 mmol) dissolved in 40 ml of absolute methanol were mixed to 0.5 g of Dowex 50 ($H^+$) resin. The mixture was refluxed during 48 hours under constant stirring. The analytical determination with resorcinol HCl and thiobarbituric acid (TBA) showed that at 24 and 48 hours the 85% and 97% of sialic acid was converted into Intermediate 1, respectively. The resin was then filtered off on current paper filter and the elute was concentrated to dryness by means of a rotary evaporator to yield an oily yellowish liquid. The oily liquid was then recovered with a reduced volume of a mixture of ethyl ether:methanol (3:1 w/w). The solution was kept standing during 24-48 hours at 4° C. and a crystalline precipitate was recovered by filtration and dried on $P_2O_5$. 145 mg of solid Intermediate 1 (M.W. 337.4) were obtained (Yield: 60.0%).

The resulting Intermediate 1 resulted positive to resorcinol-HCl reaction (with the same intensity as sialic acid) and negative to TBA reaction.

Example 2

Preparation of Intermediate 2

145 mg of Intermediate 1 (0.43 mmol) were dissolved in 10.7 ml of a 0.06 M aqueous solution of sodium hydroxide and constantly stirred at room temperature during 2-3 hours. The mixture was then adjusted to pH 7.0-7.5 with Dowex 50 ($H^+$) resin. The resin was filtered off and the elute was lyophilized to yield a whitish solid. 132.6 mg of solid Intermediate 2 (M.W. 323.3) were obtained (Yield: 95.0%).

The resulting Intermediate 2 resulted positive to resorcinol-HCl reaction (with the same intensity as sialic acid) and negative to TBA reaction.

Example 3

Preparation of Intermediate 3

132.6 mg (0.41 mmol) of lyophilized solid (Intermediate 2) were dissolved in 4.3 ml of distilled water. An aliquot of 10.7 ml of an aqueous solution of 0.038 M sodium metaperiodate ($NaIO_4$) (0.41 mmol) was then added (molar ratio=1:1) and the solution which was kept during 1 hour in darkness at room temperature under constant stirring. 12.8 ml of an aqueous solution of 0.1 M barium acetate were added to the mixture to precipitate the excess of iodate and periodate. The mixture was filtered using a current paper filter. The elute was saturated bubbling carbon dioxide to precipitate the excess of barium acetate and then filtered off on a paper filter. The elute was lyophilized to yield a slightly yellowish solid. 101.9 mg of solid Intermediate 3 (M.W. 291.3) were collected (Yield: 85.0%).

The resulting Intermediate 3 resulted positive to resorcinol-HCl reaction (with the same intensity as sialic acid) and negative to TBA reaction.

Example 4

Preparation of Intermediate 4

132.6 mg (0.41 mmol) of lyophilized solid (Intermediate 2) were dissolved in 4.3 ml of distilled water. 10.7 ml of an aqueous solution of 0.2 M sodium metaperiodate ($NaIO_4$) (2.14 mmol) (molar ratio: 1:5.24) and was added to the solution which was kept under constant stirring at room temperature during 1 hour in darkness.

12.8 ml of an aqueous solution of 0.1 M barium acetate were added to the mixture to precipitate the excess of iodate and periodate. The mixture was filtered using current paper filter. The elute was saturated bubbling carbon dioxide to precipitate the excess of barium acetate and then filtered off on a paper filter. The elute was lyophilized to yield a slightly yellowish solid. 91.4 mg of solid Intermediate 4 (M.W. 261.23) were collected (Yield: 85.0%).

The resulting Intermediate 4 resulted positive to resorcinol-HCl reaction (with the same intensity as sialic acid) and negative to TBA reaction.

Example 5

Preparation of Intermediate 5

91.43 mg (0.35 mmol) of lyophilized powder Intermediate 4 were dissolved in 2.0 ml of an aqueous solution of 2.3 mM formic acid at a pH of about 4.0. The solution was heated to 80° C. during 1 hour. The solution was then lyophilized.

72.76 mg of Intermediate 5 (M.W. 247.20) were obtained (Yield: 84.1%).

The resulting Intermediate 5 was positive both to resorcinol-HCl and TBA reactions.

Example 6

Preparation of Intermediate 6

101.96 mg (0.35 mmol) of lyophilized solid Intermediate 3 were dissolved in 2.0 ml of an aqueous solution of 2.3 mM formic acid at a pH of about 4.0. The solution was heated to 80° C. during 1 hour. The solution was then lyophilized.

93.83 mg of Intermediate 6 (M.W. 277.23) were obtained (Yield: 96.7%).

The resulting Intermediate 6 was positive both to resorcinol-HCl and TBA reactions.

Example 7

Preparation of Compound 1

84.0 mg (0.34 mmol) of lyophilized solid (Intermediate 5) were dissolved in 5.0 ml of distilled water. Thereafter 51.442 mg of amantadine (0.34 mmol) were added under slow stirring. The mixture was kept overnight under slow stirring and at 4° C. After addition of 40.0 mg of sodium borohydride, the reaction mixture was kept during 1 hour under stirring at room temperature. The mixture was then passed on a column with Dowex 50 ($H^+$) resin to convert the excess of sodium borohydride into boric acid. The elute was lyophilized. The lyophilized solid was then recovered with a small aliquot of methanol and the elute was brought to dryness. This operation was repeated at least three times. The dried solid was finally recovered with a small aliquot of water and then lyophilized to yield the final Compound 1.

110.53 mg of Compound 1 (M.W. 382.45) were obtained (Yield: 85.0%).

Figure 1:
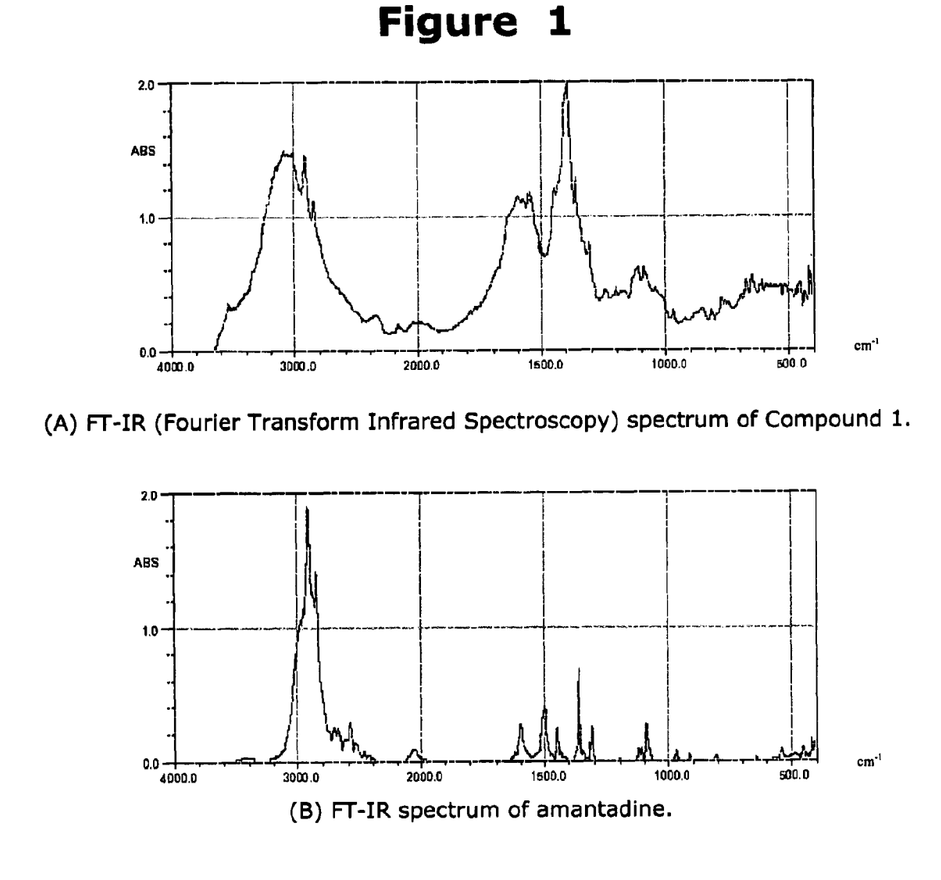
FIG. 1 is a FT-IR (Fourier Transform Infrared Spectroscopy) spectrum (A) of Compound 1, compared to that of the starting intermediate amantadine (B)

The collected Compound 1 was positive both to resorcinol-HCl reaction and TBA reaction. The FT-IR (Fourier Transform Infrared Spectroscopy) spectrum (A) of Compound 1, drawn in FIG. 1, compared to that (B) of the starting intermediate amantadine, shows the following references: a) amide I band: 1640 $cm^{-1}$; b) amide II band: 1550 $cm^{-1}$; c) primary amino groups: 600-800 $cm^{-1}$, 1590-650 $cm^{-1}$, 3330-3380 $cm^{-1}$; secondary amino groups: 700-800 $cm^{-1}$; 1615 $cm^{-1}$; 3300 $cm^{-1}$.

Example 8

Preparation of Compound 2

94.26 mg (0.34 mmol) of lyophilized solid (Intermediate 6) were dissolved in 5.0 ml of distilled water. Thereafter 82.7 mg of ribavirine (0.34 mmol) were added under slow stirring. The mixture was kept overnight at 4° C. under slow stirring. After addition of 40.0 mg of sodium borohydride the reaction mixture was kept during 1 hour under stirring and at room temperature. The mixture was then passed on a column Dowex 50 ($H^+$) resin to convert the excess of sodium borohydride into boric acid. The elute was lyophilized. The lyophilized was then recovered with a small aliquot of methanol and the elute was brought again to dryness. This operation was repeated at least three times. The dried solid was finally dissolved with a small aliquot of water and then lyophilized to yield a solid (Compound 2). 94.02 mg of solid Compound 2 (M.W. 505.4) were collected (Yield: 89.0%).

The collected Compound 2 was positive both to resorcinol-HCl and TBA reactions.

Example 9

Preparation of Compound 3

94.26 mg (0.34 mmol) of lyophilized solid (Intermediate 6) were dissolved in 5.0 ml of distilled water. Thereafter 51.442 mg of amantadine (0.34 mmol) were added under slow stirring. The mixture was kept overnight at 4° C. under slow stirring. After addition of 40.0 mg of sodium borohydride the reaction mixture was kept at room temperature under stirring during 1 hour. The mixture was then passed on a Dowex 50 ($H^+$) column in order to convert the excess of sodium borohydride into boric acid. The elute was lyophilized. The lyophilized solid was then dissolved in a small aliquot of methanol and the filtrate was brought to dryness. This operation was repeated at least three times. The dried solid was then dissolved in a small aliquot of water and then lyophilized to afford the final Compound 3. 122.02 mg of solid Compound 3 (M.W. 412.5) was collected (Yield: 87.0%).

The collected Compound 3 was positive both to resorcinol-HCl and TBA reactions.

Example 10

Preparation of Compound 4

84.0 mg (0.34 mmol) of lyophilized solid (Intermediate 5) were dissolved in 5.0 ml of distilled water. Thereafter 60.962 mg of rimantadine (0.34 mmol) were added under slow stirring. The mixture was kept overnight at 4° C. under slow stirring. After addition of 40.0 mg of sodium borohydride the reaction mixture was kept at room temperature under stirring during 1 hour. The mixture was then passed on a Dowex 50 (H+) column to convert the excess of sodium borohydride into boric acid. The elute was lyophilized. The lyophilized solid was then recovered with a small aliquot of methanol and the elute was brought to dryness. This operation is repeated at least three times. The dried powder is then dissolved with a small aliquot of water and then lyophilized to yield the final Compound 4.

125.61 mg of Compound 4 (M.W. 410.5) were collected (Yield: 90.0%).

Figure 2:
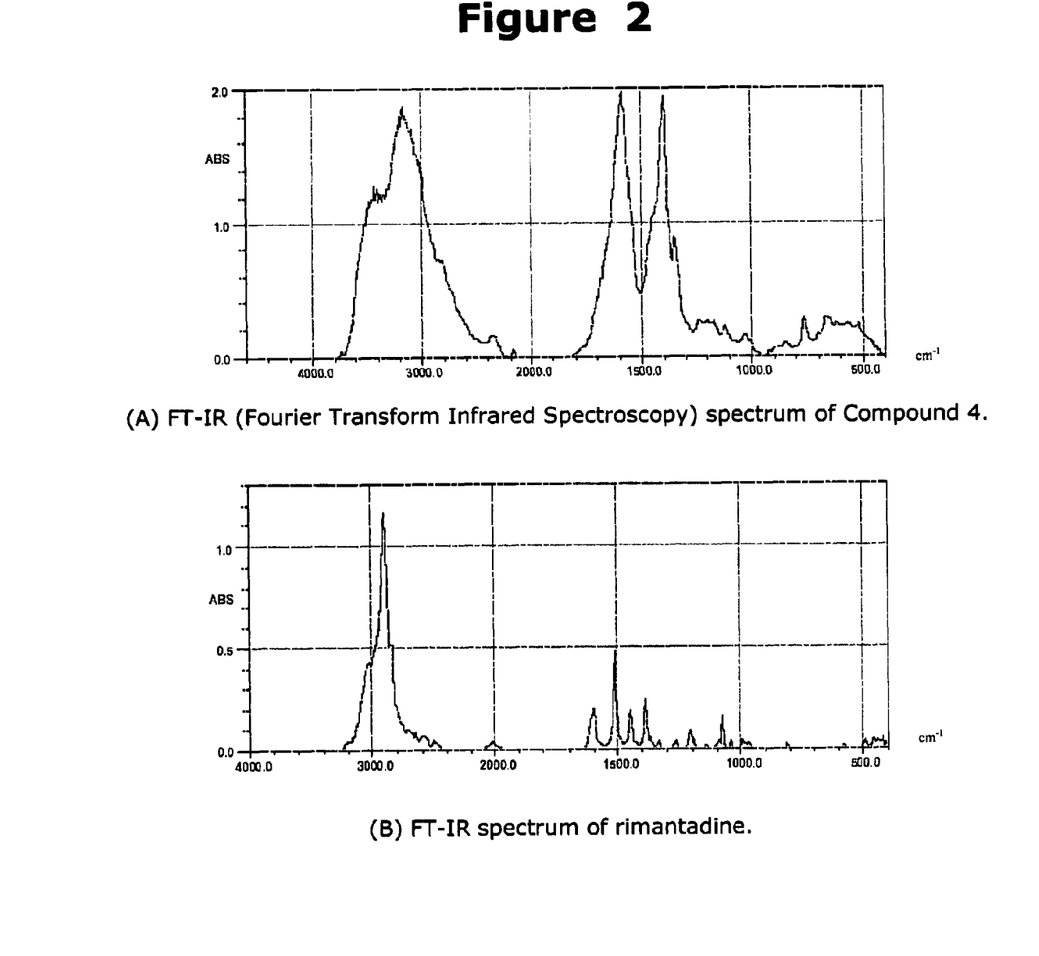
FIG. 2 is a FT-IR spectrum (A) of Compound 4, compared to that of the starting intermediate rimantadine (B)

The collected Compound 4 was positive both to resorcinol-HCl reaction and to TBA reaction. The FT-IR spectrum (A) of Compound 4, drawn in FIG. 2, compared to that (B) of the starting intermediate rimantadine, shows the following references: a) amide I band: 1640 $cm^{-1}$; b) amide II band: 1550 $cm^{-1}$; c) primary amino groups: 600-800 $cm^{-1}$, 1590-650 $cm^{-1}$, 3330-3380 $cm^{-1}$; secondary amino groups: 700-800 $cm^{-1}$; 1615 $cm^{-1}$; 3300 $cm^{-1}$.

Example 11

Preparation of Compound 5

94.26 mg (0.34 mmol) of lyophilized solid (Intermediate 6) were dissolved in 5.0 ml of distilled water. Thereafter 60.962 mg of rimantadine (0.34 mmol) were added under slow stirring. The mixture was kept overnight at 4° C. under slow stirring. After addition of 40.0 mg of sodium borohydride the reaction mixture was kept at room temperature under stirring during 1 hour. The mixture was then passed on a Dowex 50 (H+) column in order to convert the excess of sodium borohydride into boric acid. The elute was lyophilized. The lyophilized was then dissolved in a small aliquot of methanol and the elute was brought to dryness. This operation was repeated at least three times. The dried solid was then dissolved with a small aliquot of water and then lyophilized to yield the final Compound 5. 137.79 mg of final solid Compound 5 (M.W. 440.5) were collected (Yield: 92.0%).

The collected Compound 5 was positive both to resorcinol-HCl and TBA reactions.

Example 12

Preparation of Compound 6

84.0 mg (0.34 mmol) of lyophilized solid (Intermediate 5) were dissolved in 5.0 ml of distilled water. Thereafter 70.5 mg of somantadine (0.34 mmol) were added under slow stirring. The mixture was kept overnight at 4° C. under slow stirring. After addition of 40.0 mg of sodium borohydride the reaction mixture was kept under stirring during 1 hour at room temperature. The mixture was then passed on a Dowex 50 (H+) column to convert the excess of sodium borohydride into boric acid. The elute was lyophilized. The lyophilized was then dissolved in a small aliquot of methanol and the filtrate was brought to dryness. This operation was repeated at least three times. The dried powder was then dissolved with a small aliquot of water and then lyophilized to yield the final Compound 6. 125.26 mg of solid Compound 6 (M.W. 438.6) were collected (Yield: 84.0%).

The collected Compound 6 was positive both to resorcinol-HCl and TBA reactions.

Example 13

Preparation of Compound 7

94.26 mg (0.34 mmol) of lyophilised solid (Intermediate 6) were dissolved in 5.0 ml of distilled water. Thereafter 61.0 mg of somantadine (0.34 mmol) were added under slow stirring. The mixture was kept overnight at 4° C. under slow stirring. After addition of 40.0 mg of sodium borohydride the reaction mixture was kept at room temperature under stirring during 1 hour. The mixture was then passed on a Dowex 50 (H+) column to convert the excess of sodium borohydride into boric acid. The elute was then lyophilised. The lyophilised was then dissolved in a small aliquot of methanol and the filtrate was brought to dryness. This operation was repeated at least three times. The dried powder was then dissolved with a small aliquot of water and then lyophilized to yield the final Compound 7. 135.43 mg of solid Compound 7 (M.W. 468.6) were collected (Yield: 85.0%).

The collected Compound was positive both to resorcinol-HCl and TBA reactions.

Example 14

Preparation of Compound 8

84.0 mg (0.34 mmol) of lyophilized solid (Intermediate 5) were dissolved in 5.0 ml of distilled water. Thereafter 61.0 mg of memantine (0.34 mmol) were added under slow stirring. The mixture was kept overnight at 4° C. under slow stirring. After addition of 40.0 mg of sodium borohydride the reaction mixture was kept under stirring during 1 hour at room temperature. The mixture was then passed on a Dowex 50 (H+) column to convert the excess of sodium borohydride into boric acid. The elute was lyophilized. The lyophilized was then dissolved in a small aliquot of methanol and the filtrate was brought to dryness. This operation was repeated at least three times. The dried powder was then dissolved with a small aliquot of water and then lyophilized to yield the final Compound 8. 129.80 mg of solid Compound 8 (M.W. 410.5) were collected (Yield: 93.0%).

Figure 3:
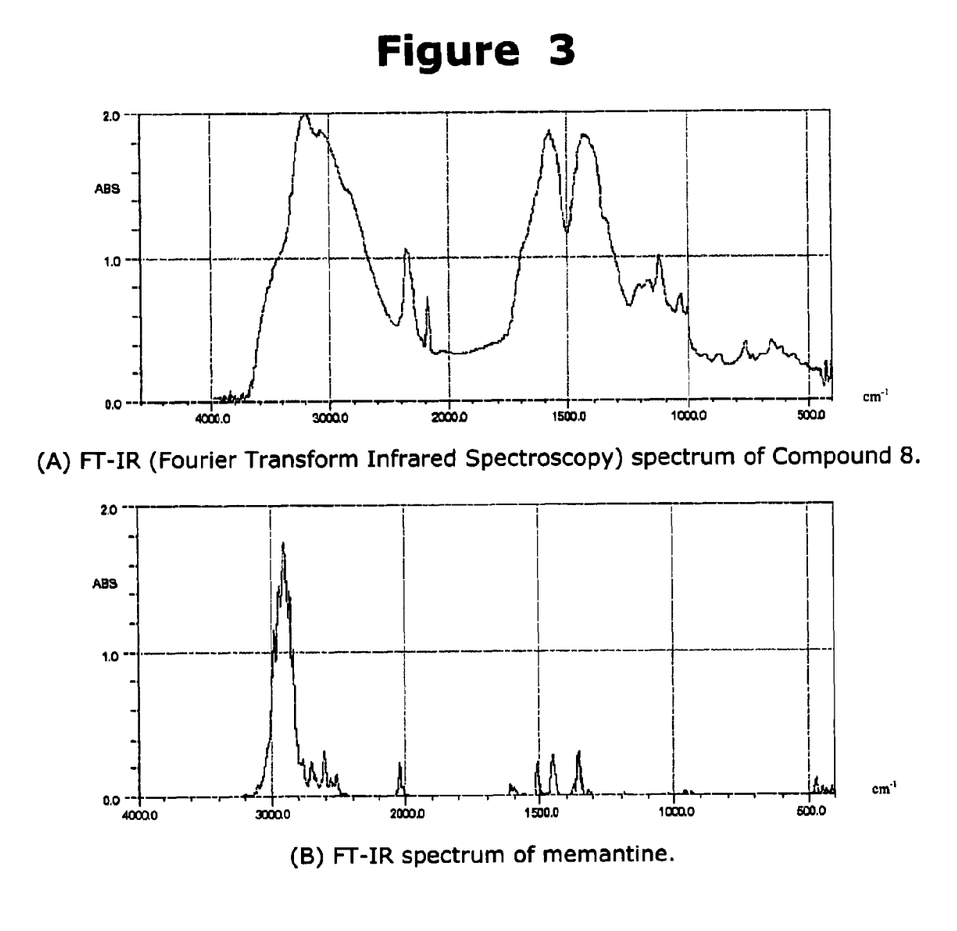
FIG. 3 is a FT-IR spectrum (A) of Compound 8, compared to that of the starting intermediate memantine (B)

The collected Compound was positive both to resorcinol-HCl and TBA reactions. The FT-IR spectrum (A) of Compound 8, drawn in FIG. 3, compared to that (B) of the starting intermediate memantine, shows the following references: a) amide I band: 1640 $cm^{-1}$; b) amide II band: 1550 $cm^{-1}$; c) primary amino groups: 600-800 $cm^{-1}$, 1590-650 $cm^{-1}$, 3330-3380 $cm^{-1}$; secondary amino groups: 700-800 $cm^{-1}$; 1615 $cm^{-1}$; 3300 $cm^{-1}$.

Example 15

Preparation of Compound 9

94.26 mg (0.34 mmol) of lyophilised solid (Intermediate 6) were dissolved in 5.0 ml of distilled water. Thereafter 61.0 mg of memantine (0.34 mmol) were added under slow stirring. The mixture was kept overnight at 4° C. under slow stirring. After addition of 40.0 mg of sodium borohydride the reaction mixture was kept at room temperature under stirring during 1 hour. The mixture was then passed on a Dowex 50 (H+) column to convert the excess of sodium borohydride into boric acid. The elute was then lyophilised. The lyophilised was then dissolved in a small aliquot of methanol and the filtrate was brought to dryness. This operation was repeated at least three times. The dried powder was then dissolved with a small aliquot of water and then lyophilized to yield the final Compound 9.

134.79 mg of Compound 9 (M.W. 440.5) were collected (Yield: 90.0%).

The collected Compound 9 was positive both to resorcinol-HCl and TBA reactions.

Example 16

Preparation of Compound 10

Figure 4:
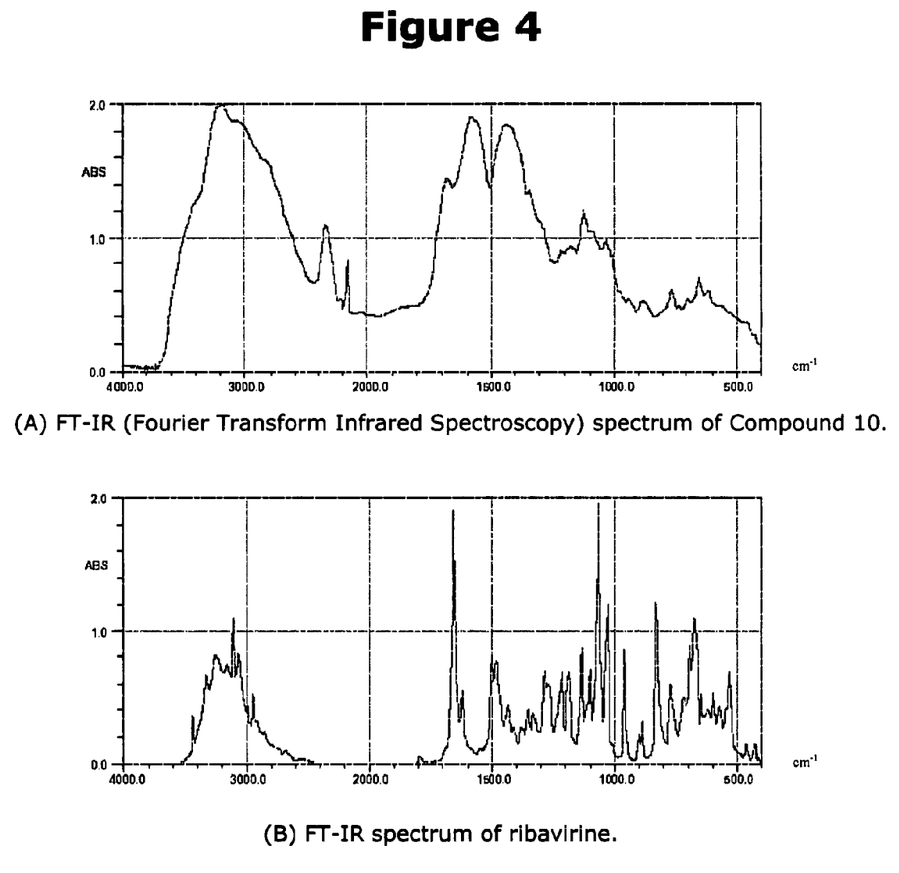
FIG. 4 is a FT-IR spectrum (A) of Compound 10, compared to that of the starting intermediate ribavirine (B).

84.0 mg (0.34 mmol) of lyophilized solid (Intermediate 5) were dissolved in 5.0 ml of distilled water. Thereafter 82.7 mg of ribavirine (0.34 mmol) were added under slow stirring. The mixture was kept overnight at 4° C. under slow stirring. After addition of 40.0 mg of sodium borohydride the reaction mixture was kept at room temperature under stirring during 1 hour. The mixture was then passed on a Dowex 50 ($H^+$) column to convert the excess of sodium borohydride into boric acid. The elute was lyophilized. The lyophilized was then dissolved in a small aliquot of methanol and the filtrate was brought to dryness. This operation was repeated at least three times. The dried powder was then dissolved with a small aliquot of water and then lyophilized to yield the final Compound 10. 140.62 mg of Compound 10 (M.W. 475.4) were collected (Yield: 87.0%). The collected Compound was positive to resorcinol-HCl and TBA reactions. The FT-IR spectrum (A) of Compound 10, drawn in FIG. 4, compared to that (B) of the starting intermediate ribavirine, shows the following references: a) amide I band: 1640 $cm^{-1}$; b) amide II band: 1550 $cm^{-1}$; c) primary amino groups: 600-800 $cm^{-1}$, 1590-650 $cm^{-1}$, 3330-3380 $cm^{-1}$; secondary amino groups: 700-800 $cm^{-1}$; 1615 $cm^{-1}$; 3300 $cm^{-1}$.

Example 17

Preparation of Compound 11

102.5 mg (0.34 mmol) of lyophilized intermediate sialic acid were dissolved in 50.0 ml of mixture of methanol:distilled water (9:1, v/v) Thereafter 51.442 mg of amantadine (0.34 mmol) were added under slow stirring. After addition of 100.0 mg of sodium borohydride the reaction mixture was kept at 60° C. under stirring during 1 hour. The mixture was then passed on a Dowex 50 ($H^+$) column in order to convert the excess of sodium borohydride into boric acid. The elute was lyophilized. The lyophilized was then dissolved in a small aliquot of methanol and the filtrate was brought to dryness. This operation was repeated at least five times. The dried solid was then dissolved with a small aliquot of water and then lyophilized to yield the final Compound 11. A total of 133.90 mg solid Compound 11 (M.W. 442.5) were collected (Yield: 89.0%). The collected compound was positive to resorcinol-HCl reaction and negative to TBA reaction.

Example 18

Antiviral Activity Evaluation of the Invention Compounds Against Strains of Influenza Viruses of Type A and B Objective and Study Plan In particular, the in vitro antiviral activity against influenza viruses type A and B of the Compound 1 and the Compound 8 compared to adamantine and memantine, two compounds of appreciate antiviral activity, has been evaluated. For the study, two isolated of influenza viruses type A and an isolated viral type B have been used.

Materials and Methods

1—Propagation and Titration of Influenza Viruses

The strains of influenza viruses A/H3N2 (A/Panama/2007/99), A/H1N1 (A/New Calcdonia/20/99) and B (B/Shandong/7/97) have been spread into embryonic chicken-eggs. In short, the influenza virus strains have been inoculated, by allantoid route, in chicken eggs fecundated since 11 days. Therefore the eggs have been incubated at 37° C. during 3 days, and the allantoic liquid has been collected and subsequently titred.

The determination of the assay has been carried out by plaque formation test (Plaque Assay, PA). Particularly, serial dilutions ($10^{-1}$-$10^{-11}$) of each isolated viral have been inoculated on a confluent monolayer of MDCK (Madin-Darby Canine Kidney) cells in plates with 12 wells. After incubation during 1 hour at 37° C., the viral inoculate has been removed and infection medium (MEM (Minimum Essential Medium) containing 10 µg/ml trypsin, 2% agar) has been added. After 3 days of incubation at 37° C., 5% $CO_2$, the monolayers of cells have been fixed with a 5% glutaraldehyde solution and, after agar removal, have been coloured with a solution of 5% carbol-fuchsin.

The plaques have been visually counted and the isolated assay has been expressed by number of Plaque Forming Unit (PFU) per ml (PFU/ml).

2—Evaluation of Antiviral Activity of Compound 1 and Compound 8 in Relation to Amantadine and Memantine.

2.1. Preparation of Compounds to be Analyzed

The Compounds 1 and 8, after been dried during 72 hours, and the comparable compounds amantadine and memantine have been suitably reconstituted in sterile distilled water at a concentration of 1000 µM. Later on serial dilutions, on basis 10, in a range from 0.01 µM to 100 µM for each compound under test have been carried out.

2.2. Plaque Reduction Assay (PRA)

Confluent monolayers of MDCK cells, grown in plates with 12 wells ($1 \times 10^5$ cells/ml) have been infected with about 50 PFU/ml of each isolated viral (A/Panama/2007/99-H3N2, A/New Calcdonia/20/99-H1N1 and B/Shandong/7/97). After incubation during 1 hour at 37° C., 5% $CO_2$, in order to permit the viral adsorption, the viral inoculate has been removed and the cellular monolayers have been washed twice with MEM culture medium. An overlay-medium has been added (10 µg/ml trypsin, 2% agar in MEM) to each well containing serial dilutions (from 0.01 µM to 100 µM) of the compounds under analysis. The test has been carried out in duplicate and simultaneously a reaction control not containing the antiviral compound has been added. The cell cultures have been thus incubated at 37° C., 5% $CO_2$ during 3 days. Subsequently, the cellular monolayers have been fixed by using 5% glutaraldehyde solution and incubated during at least 3 hours at room temperature, in order to promote the penetration into the agar. After agar removal, the cellular monolayers have been coloured with a 5% carbol-fuchsin solution. The plaques have been visually counted and the degree of plaques inhibition has been calculated in relation to the controls not containing the compounds under test. Thus the concentration of the compound necessary to reduce the plaques number to 50% against the control without the compound has been determined.

Results

The antiviral activity of Compound 1 and Compound 8 and of the control compounds amantadine and memantine has been evaluated by a Plaque Reduction Assay (PRA) using MDCK cells. The results are shown in Table 1.

Compound 1 exhibited similar activity to amantadine against virus type A H3N2, but 10 fold less activity against virus type A H1N1. The antiviral activity of Compound 1 against influenza virus type B resulted in higher than (>10 folds) activity than that of amantadine (>100 μM) (Table 1).

Compound 8 exhibited antiviral activity of the order of 10 fold more than memantine against the analyzed influenza viruses of type A (A/H3N2 and A/H1N1). Any antiviral activity of Compound 8 has been evidenced against influenza virus type B in the tested concentration range (Table 1).

TABLE 1

| Virus | Compounds (μM) | | | |
| --- | --- | --- | --- | --- |
|  | Compound 1 | Amantadine | Compound 8 | Memantine |
| A/Panama/2007/99-H3N2 | 10 | 10 | 10 | 100 |
| A/NewCaledonia/20/99-H1N1 | 1 | 0.1 | 10 | 100 |
| B/Shandong/7/97 | 10 | >100 | >100 | 100 |

CONCLUSIONS

The data therefore provides evidence of an enhanced antiviral activity of Compound 1 against influenza virus type B compared to adamantine. It must be borne in mind that adamantine acts by blocking the M2 protein of ion channels present only in the influenza virus type A, but not in the type B and therefore it could be a new mechanism of action that will be the object of future studies.

Compound 8 exhibited antiviral activity 10 fold higher than memantine against influenza viruses of type A.

The invention claimed is:

1. A compound of structural formula (I):

(I)

wherein:
X is —CH$_2$— or —O—;
a single or double bond links C$_2$ to C$_3$ of the ring;
R$^1$ denotes —OH, a halogen or —B/moiety, but with the proviso that R$^1$ is absent when a double bond linking C$_2$ to C$_3$ of the ring is present;
R$^2$ is —OH, —O—CH(C$_2$H$_5$)$_2$, —NH$_2$, —NHC(═NH)NH$_2$ or —NH—OH;
R$^3$ is —NH$_2$, —NHCO—CH$_3$ or —NH—CO-CH$_2$—OH; and
R$^4$ is —CHOH—CHOH—CH$_2$—OH, —CHOH—CH$_2$B/moiety, —CH$_2$—B/moiety or —B/moiety;
with the proviso that at least one of R$^1$ or R$^4$ contains a —B/moiety, or both R$^1$ and R$^4$ contain a —B/moiety;

wherein said —B/moiety is:

and wherein:
R$^5$ is —NH—, —CH$_2$—NH—, —CH(CH$_3$)—NH—, —NH—CH(CH$_3$)—NH—, —C(CH$_3$)$_2$—CH$_2$—NH—, —NH—CO—CH$_2$—O—CH$_2$—CH$_2$—NH—, R$^6$ is —H, —CH$_3$ or —C$_2$H$_5$;
R$^7$ is —H, —CH$_3$ or —C$_2$H$_5$; and
R$^8$ is —NH—, —CO—NH— or —C(NH)—NH—; and addition salts, resolved enantiomers or purified diastereomers thereof.

2. The compound of claim 1 wherein R$^4$ is —CHOH—CH$_2$B/moiety or —CH$_2$—B/moiety, and the compound is selected from the group consisting of:

Compound 1

Compound 2

Compound 3

-continued

Compound 4

Compound 5

Compound 6

Compound 7

Compound 8

Compound 9

-continued

Compound 10

3. The compound as claimed in claim 1, wherein $R^1$ is —B/moiety, and the compound is selected from the group consisting of:

and

4. The compound of claim 1, wherein $R^1$ is —B1/moiety, and $R^4$ is —CHOH—CH$_2$B1/moiety, the compound is as follows:

5. The compound of claim 1, wherein $R^1$ is —B2/moiety, and $R^4$ is —CHOH—CH$_2$B2/moiety, and the compound is as follows:

6. The compound of claim 1, wherein $R^1$ is —B1/moiety and $R^4$ is —CHOH—CH$_2$B2/moiety, or $R^1$ is —B2/moiety and $R^4$ is —CHOH—CH$_2$B1/moiety, and the compound is selected from the group consisting of:

7. A pharmaceutical composition, comprising:

the compound as in one of claims 1 to 6, or mixtures thereof, in a pharmaceutically acceptable carrier.

8. The compound of claim 1 for treatment of a viral infection caused by at least one of: a hemagglutinin (HA) containing virus, a neuraminidase (NA) containing virus, or a $M_2$ protein containing virus, wherein the infection is caused by influenza viruses type A or B.

9. A medicament for treating a viral infection caused by a hemagglutinin (HA) and/or neuraminidase (NA) containing virus and/or $M_2$ protein containing virus, wherein the infection is caused by influenza viruses type A or B, comprising:

a therapeutically effective amount of the compound of claim 1.

10. A RNAm-quanilyltransferase-inhibiting compound according to claim 1 for treating a disease or condition mediated by RNAm, RNA polymerase and enzyme RNAm-guanilyltransferase, wherein the RNAm, RNA polymerase and enzyme RNAm-guanilyltransferase mediated disease or condition is hepatitis virus type C (HVC) infection.

11. The pharmaceutical composition of claim 7, further comprising:

a compound active against influenza viruses type A for treatment of a viral infection caused by at least one of: a hemagglutinin (HA) containing virus, a neuraminidase (NA) containing virus or an $M_2$ protein containing virus, wherein the infection is caused by influenza viruses type A or B.

12. A pharmaceutical composition, comprising:

the compound of claim 10; and a compound active against hepatitis virus type C (HVC) for treatment of a disease or condition mediated by RNAm and RNA polymerase, wherein the RNAm and RNA polymerase mediated disease or condition is hepatitis virus type C (HVC) infection.

* * * * *